United States Patent
Crye et al.

(10) Patent No.: US 6,920,646 B2
(45) Date of Patent: Jul. 26, 2005

(54) HUMAN WASTE MANAGEMENT SUIT

(75) Inventors: Caleb Clark Crye, Brooklyn, NY (US); Gregg M. Thompson, Brooklyn, NY (US); Eric Owen Fehlberg, Queens, NY (US)

(73) Assignee: LineWeight LLC, Brooklyn, NY (US)

( * ) Notice: Subject to any disclaimer, the term of this patent is extended or adjusted under 35 U.S.C. 154(b) by 121 days.

(21) Appl. No.: 10/601,322

(22) Filed: Jun. 21, 2003

(65) Prior Publication Data

US 2005/0076423 A1 Apr. 14, 2005

(51) Int. Cl.[7] ............................................... A62B 17/00
(52) U.S. Cl. .......................................... 2/457; 604/348
(58) Field of Search ............................ 2/456, 457, 458, 2/901, 2.11, 2.14, 2.15; 604/327, 348

(56) References Cited

U.S. PATENT DOCUMENTS

| | | | | | |
|---|---|---|---|---|---|
| 3,034,131 A | * | 5/1962 | Constantin | ..................... | 2/2.14 |
| 4,274,159 A | * | 6/1981 | Schmidt | ........................ | 2/227 |
| 4,820,291 A | * | 4/1989 | Terauchi et al. | ............ | 604/349 |
| 5,032,118 A | * | 7/1991 | Mason | ........................ | 604/349 |
| 5,210,879 A | * | 5/1993 | Miller | ............................. | 2/82 |
| 5,334,174 A | * | 8/1994 | Street | ......................... | 604/313 |
| 6,209,144 B1 | * | 4/2001 | Carter | ............................ | 2/458 |
| 6,296,627 B1 | * | 10/2001 | Edwards | .................... | 604/347 |
| 6,363,531 B1 | * | 4/2002 | Quinn | ............................ | 2/82 |

* cited by examiner

Primary Examiner—Rodney M. Lindsey
(74) Attorney, Agent, or Firm—Stiennon & Stiennon

(57) ABSTRACT

A chemical/biological hazard protection suit has two pants legs which extend to a midsection below waist level. An opening in the midsection defines an outlet from the suit interior. A waste collector has an upper segment which is fixed to the midsection and which adjoins an intermediate segment which is in turn connected to a waste receptacle. A first seal is between the upper segment and the intermediate segment, and a second seal is between the intermediate segment and the waste receptacle. A region of weakened material encircles the intermediate segment between the seals. A wearer discharges waste through the outlet and past the two open seals into the receptacle, whereupon both seals are closed, and the receptacle is detached from the upper segment, leaving both the receptacle and the suit sealed. Prior to use, the waste receptacle may be retained within a pocket on one of the pants legs.

13 Claims, 4 Drawing Sheets

HUMAN WASTE MANAGEMENT SUIT

STATEMENT AS TO RIGHTS TO INVENTIONS MADE UNDER FEDERALLY SPONSORED RESEARCH AND DEVELOPMENT

The U.S. Government has a paid-up license in this invention and the right in limited circumstances to require the patent owner to license others on reasonable terms as provided for by the terms of contract No. DAAD16-01-C-0061 awarded by the U.S. Army Robert Morris Acquisition Natick Contracting Division of the U.S. Department of Defense.

CROSS REFERENCES TO RELATED APPLICATIONS

Not applicable.

BACKGROUND OF THE INVENTION

The present invention relates to chemical/biological hazard protection suits for military, public safety, and industrial applications.

Many environments pose immediate threats to the life or health of those who enter them. Whether as a result of chemical agents intentionally or unintentionally released through industrial processes, biological hazards found in contaminated regions, or chemical or biological substances specifically introduced in the course of warfare or terrorism, areas exist which are extremely hazardous to humans. Nevertheless, it is often essential that operators, officials, or soldiers be able to enter these contaminated regions at will.

Chemical/biological hazard protection suits form a sealed environment which surrounds the wearer and prevents the infiltration of the dangerous agents. A variety of hazard protection suits have been developed, some specialized for civilian or military applications. Advances in fabric and suit design have made it possible for operators to reside within a hazard suit for extended periods of time without overheating. However, long-duration operation within a hazard suit introduces its own problems. Occupancy which extends into a length of hours may present the wearer with annoying or debilitating discomfort unless some provision is made for the relief of the operator by urination or defecation.

However, unless the wearer can be removed from the hazardous region, it is not possible to breach the seal of the hazard protection suit without compromising the safety of the wearer.

What is needed is a chemical/biological hazard protection suit which will permit the relief of the occupant without exposing the occupant to environmental hazards.

SUMMARY OF THE INVENTION

The chemical/biological hazard protection suit of this invention is formed of contaminant impervious material and has two pants legs which extend to a midsection below waist level. An opening in the midsection defines an outlet from the suit interior. A waste collector is affixed to the midsection of the suit and seals the outlet. The waste collector has an upper segment which is fixed to the midsection and which adjoins an intermediate segment which is in turn connected to a waste receptacle. A first seal is positioned between the upper segment and the intermediate segment, and a second seal is positioned between the intermediate segment and the waste receptacle. A region of weakened material encircles the intermediate segment between the first and second seals. A wearer discharges waste through the outlet and past the two open seals into the receptacle, whereupon both seals are closed, and the receptacle is detached from the upper segment, leaving both the receptacle and the suit sealed. Prior to use, the waste receptacle, still attached to the suit outlet, may be retained within a pocket on one of the pants legs.

It is a feature of the present invention to provide a chemical/biological hazard protection suit which may be comfortably worn for extended periods.

It is another feature of the present invention to provide a chemical/biological hazard protection suit which permits the wearer to discharge bodily wastes from the suit without being exposed to the exterior environment.

Further objects, features and advantages of the invention will be apparent from the following detailed description when taken in conjunction with the accompanying drawings.

DESCRIPTION OF THE PREFERRED EMBODIMENTS

Figure 1:
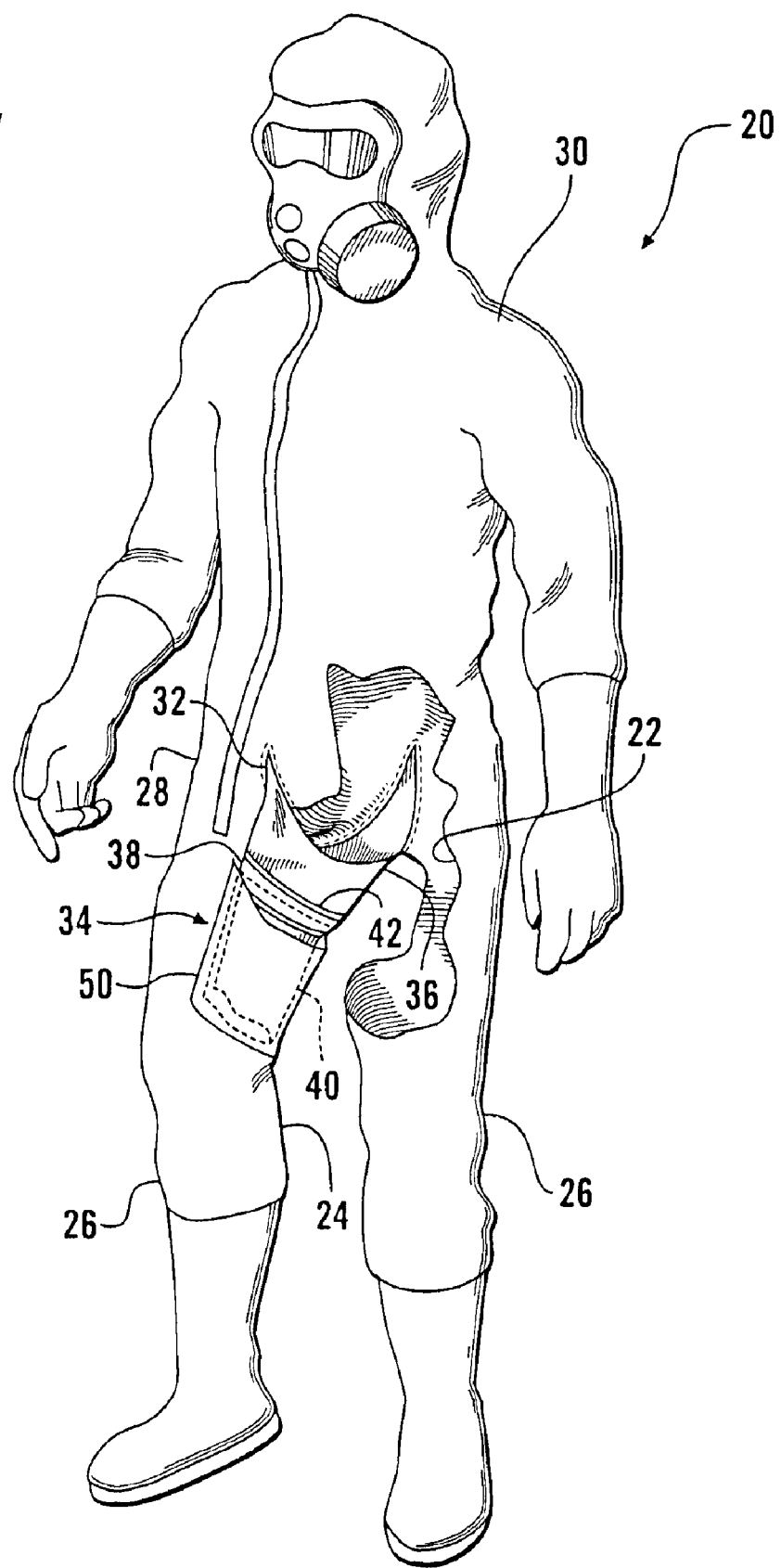
FIG. 1 is a perspective view of the chemical/biological hazard protection suit of this invention, partially broken away in section to reveal the waste collector. The suit is shown with the waste receptacle in a stowed position.

Referring more particularly to FIGS. 1–4, wherein like numbers refer to similar parts, a chemical/biological hazard protection suit 20 is shown in FIG. 1. The suit 20 may be fabricated of conventional chemical/biological hazard suit material such as selectively permeable membrane material, and may incorporate conventional features of such suits which promote exchange of water vapor, and cooling air circulation. In addition, the suit 20 may include features which permit it to be donned rapidly, such as in the hazard protection suit disclosed in our co-pending U.S. patent application Ser. No. 10/255,569, filed Jun. 19, 2003, the disclosure of which is incorporated by reference herein.

The suit 20 has a sealed interior 22 defined inwardly of a pants section 24 having two pants legs 26 which extend upwardly to a midsection 28. An upper section 30 extends upwardly from the midsection, and includes a torso-covering section, sleeves, gloves, and a hood with a respirator mask.

Figure 3:
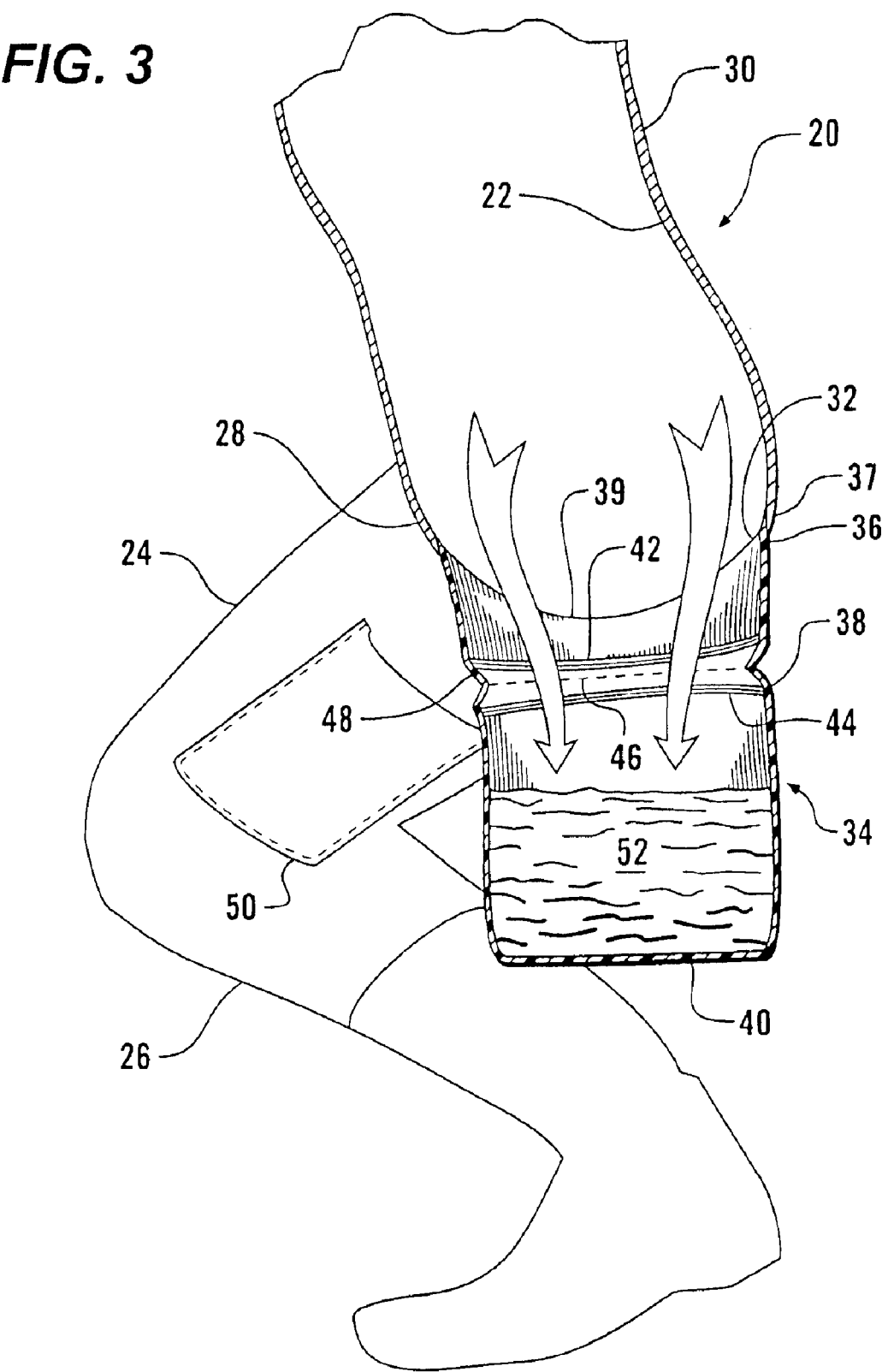
FIG. 3 is a cross-sectional view of the chemical/biological hazard protection suit of FIG. 2 in the process of collecting waste.

At a lower level of the suit midsection 28, between the pants legs 26, an outlet 32 is formed in the suit which communicates with a waste collector 34. As best shown in FIG. 3, the outlet 32 is an opening which stretches from front to back between the two pants legs 26 of the suit. The waste collector 34 is fixed to the midsection 28 so as to receive human waste such as urine and feces which are discharged through the outlet 32. The waste collector 34 may be formed of a flexible plastic material, for example a non-woven fabric, such as TYVEK® nonwoven spunbonded olefin sheets or TYCHEM® material manufactured by E.I. du Pont de Nemours and Company, or other impermeable yet flexible material. The waste collector 34 may be assembled from two sheets of material fused along edge seams, or it may be formed as a continuous tube of material.

The waste collector 34 has an upper segment 36 which is permanently fixed to the midsection 28 of the suit to receive waste discharged through the outlet 32. The upper segment 36 has two flaps 37, best shown in FIG. 3, each of which is fastened to the suit adjacent the outlet. Each flap 37 has a concave curved upper edge 39 which conforms to the shape of the underside of the suit midsection 28. An intermediate segment 38 extends outwardly from the upper segment 36 to join a waste receptacle 40. The front to back dimension of the waste receptacle is about twelve inches, and the vertical dimension of the waste collector is about 12–18 inches. A first closable seal 42 extends across the waste collector between the upper segment 36 and the intermediate segment 38. A second closable seal 44 extends across the waste collector between the intermediate segment 38 and the waste receptacle 40. The first closable seal 42 and the second closable seal 44 are formed of mating plastic members which are closable by the application of pressure thereto. The seals 42, 44, for example, may be of the ZIPLOK® grip seal or rail lock type manufactured by S. C. Johnson & Son, Inc. A separation region is defined between the first seal 42 and the second seal 44 by a region of weakened material 46. The region of weakened material 46 may be formed by heat or pressure or other technique to define a line of material which is readily severed when it is desired to separate the waste receptacle from the suit. The intermediate segment may be formed with a small wedge-shaped relief 48 at the terminations of the region of weakened material 46 to assist the user in tearing along the region.

As shown in FIG. 1, the suit 20 is preferably formed with an upwardly opening storage pocket 50 on one of the two pants legs 26. The storage pocket 50 is formed by a rectangular section of material which is affixed to the exterior of the pants leg 26 at a location closely spaced from the outlet 32. Prior to use, the waste receptacle 40, is received within the pocket 50. Because the waste receptacle 40 is formed of lightweight and thin flexible material, it is conveniently kept out of the way of the wearer while stored within the pocket 50. If the pocket is not as wide as the waste collector, the waste collector may be folded to fit within the pocket 50. During the initial period of wear, the waste receptacle 40 remains within the pocket, and both the first seal 42 and the second seal 44 are open. However, the waste receptacle 40 is a closed bag, and there is thus an impervious barrier to contaminants entering the suit 20 through the collector 34.

Figure 2:
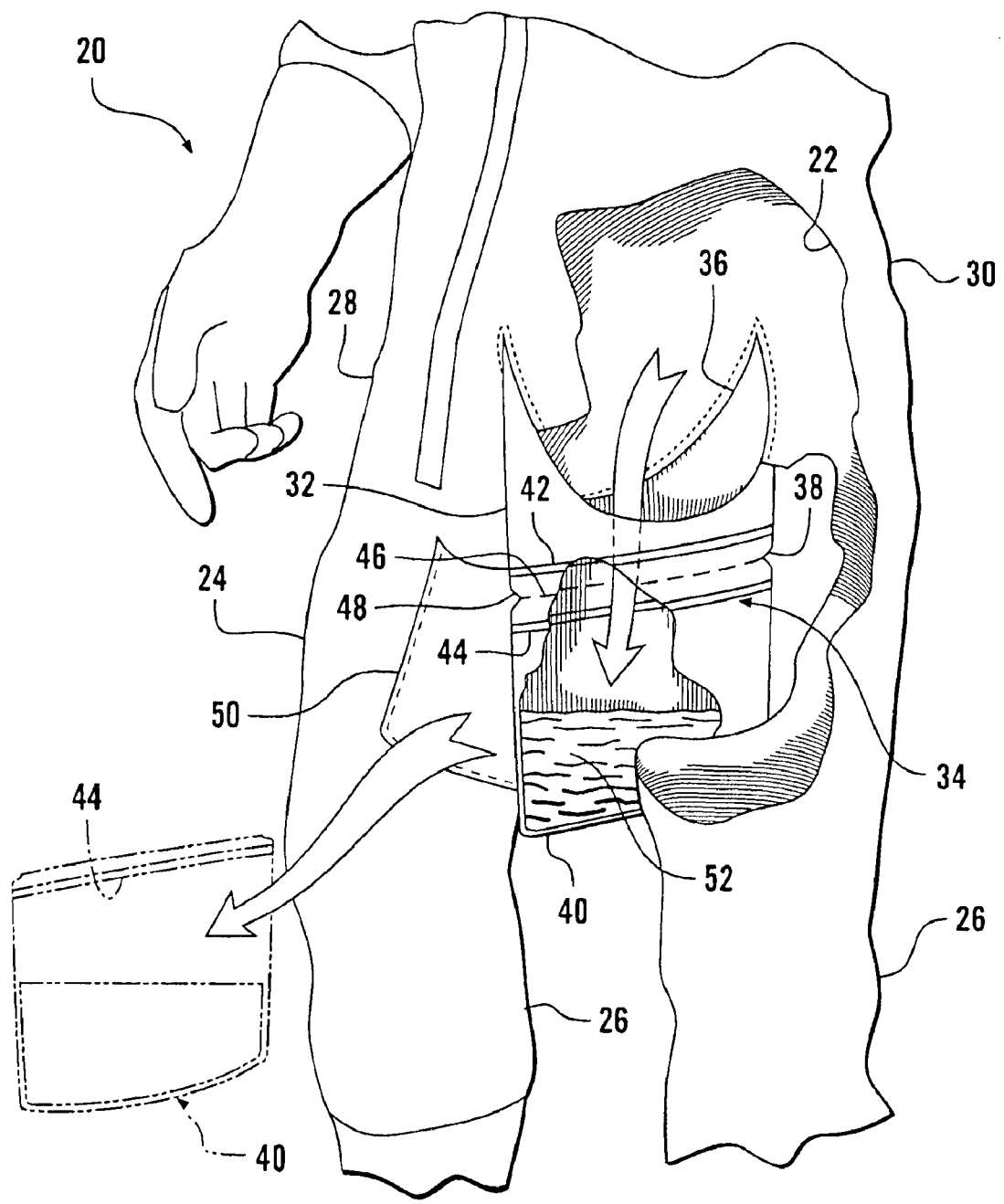
FIG. 2 is a perspective view of the chemical/biological hazard protection suit of FIG. 1, partially broken away in section, shown in the process of collecting waste, and, in alternative view, the separation of the filled waste receptacle.

When, after the passage of time within the suit 20, the suit's wearer desires to discharge solid or liquid waste, the waste receptacle 40 is extracted from the storage pocket 50, and allowed to hang down below the outlet 32. Typically, the wearer of the suit 20 will not be wearing any undershorts beneath the suit, or will be wearing special purpose undergarments (not shown) with one or more appropriate openings for the discharge of waste. As shown in FIGS. 2 and 3, the human waste 52 flows under the force of gravity out the outlet 32, past the first seal 42, through the intermediate segment 38, and past the second seal 44 into the waste receptacle 40. Once all the waste 52 has been discharged from the suit 20, the wearer presses the first seal 42 to engage the two opposed engaging members of the seal with one another to form an air-tight closure which prevents any environmental contaminants from entering the suit through the first seal. The second seal 44 is likewise closed, thereby containing the waste 52 within the receptacle 40. Finally, the wearer tears along the region of weakened material 46 to remove the sealed waste receptacle 40 from the suit. The upper segment 36 with the sealed first seal 42 remains affixed to the suit, and the wearer may continue activities protected from chemical or biological hazards. The small portion of the waste collector that remains attached to the suit 20 is very lightweight and does not substantially interfere with the free movements of the wearer.

It will be noted that although the waste receptacle may only be detached from the waste collector once. It may be used to collect bodily wastes on several occasions before being detached from the intermediate segment. Once the waste receptacle has been detached however, for additional waste elimination activities, the wearer must return to an uncontaminated region.

Figure 4:
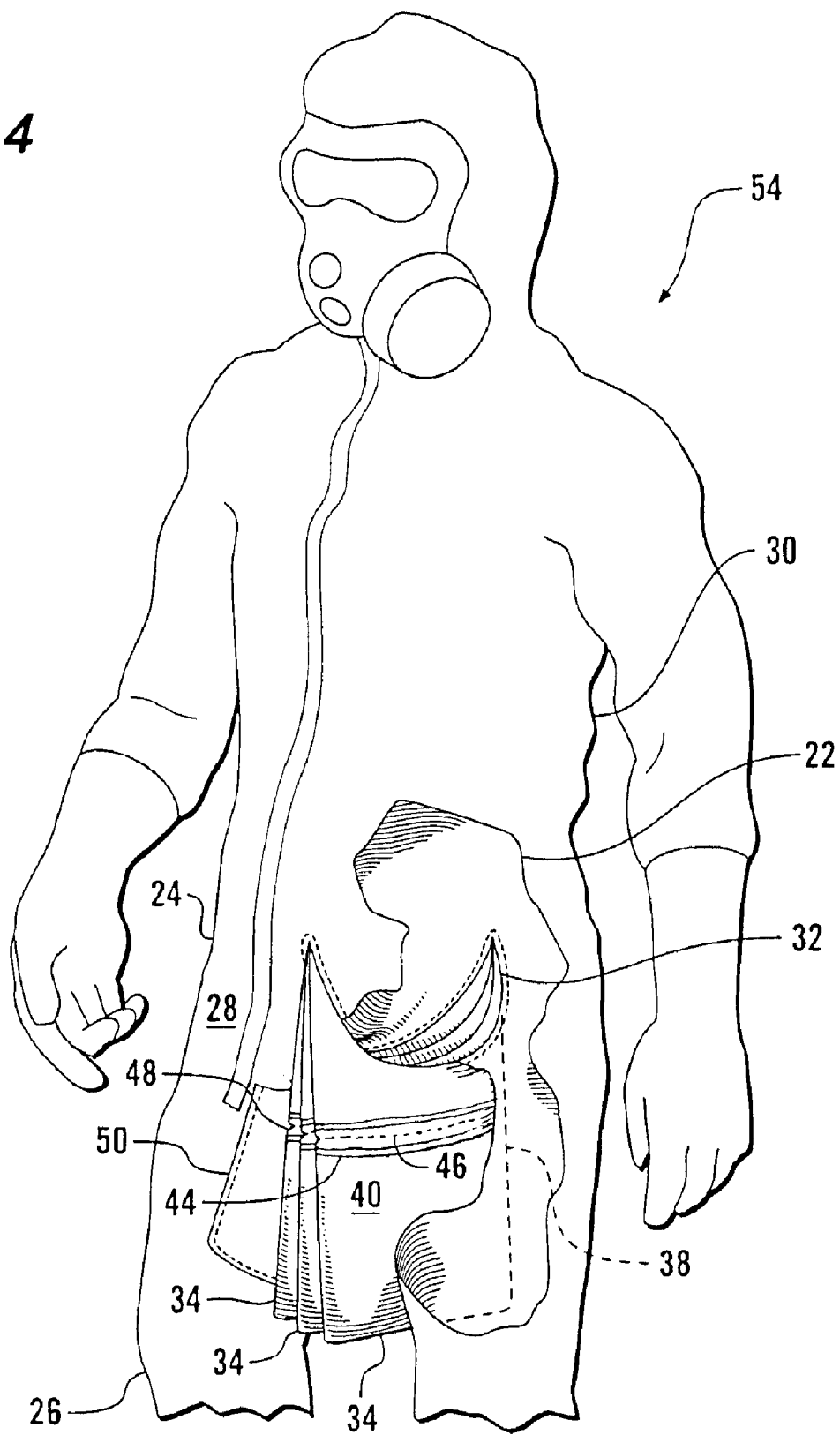
FIG. 4 is a perspective view of an alternative embodiment chemical/biological hazard protection suit of this invention having multiple waste collectors.

An alternative embodiment chemical/biological hazard protection suit 54 is shown in FIG. 4. The suit 54 is similar to the suit 20, except that multiple waste collectors 34 are fastened to the suit to communicate with the outlet 32. Two or more waste collectors 34 may be fastened to the suit outlet 32, the upper segments 36 of each waste collector being fastened to either the suit itself, or to an adjoining waste collector upper segment. Prior to use, the waste collectors 34 are stored in the leg pocket 50, one collector at a time can be extracted from the pocket as the need arises, and then the individual waste receptacles 40 can be torn off and disposed of. The suit 54 thus allows extended occupation of the hazard protection suit, without requiring a soiled waste receptacle to be carried with the suit for any length of time.

It should be noted that, although the waste receptacle 40 has been shown as transparent for illustrative purposes, it will typically be formed of an opaque flexible material. Moreover, the interior surface of the collector 34 may have the a soft toilet tissue-like surface, and may be used by the wearer of the hazard suit in a fashion similar to toilet paper. Thus the waste collector has interior portions which are soft and to serve as toilet tissue.

It is understood that the invention is not limited to the particular construction and arrangement of parts herein illustrated and described, but embraces all such modified forms thereof as come within the scope of the following claims.

We claim:

1. A hazard protection suit with provisions for waste relief, the suit having a sealed interior and comprising:

a pants section having two pants legs which extend upwardly to a midsection below waist level;

an upper section which extends upwardly from the waist level;

portions of the midsection which define an outlet from the suit interior, the outlet being positioned at a lower region of the midsection to receive discharged bodily waste and allow the passage of the waste through the outlet;

a waste collector fixed to the midsection to receive waste passing through the outlet, the waste collector having an upper segment which is fixed to the suit midsection, an intermediate section which communicates with the upper segment, and a waste receptacle which communicates with the intermediate section;

a first closable seal positioned outwardly of the suit outlet and positioned between the outlet and the intermediate section;

a second closable seal positioned between the intermediate section and the waste receptacle; and portions of the intermediate segment which define a region of weakened material which encircles the intermediate segment to permit the waste receptacle to be detached from the waste collector upper segment, such that waste is dischargeable through the suit outlet and past the first closable seal and the second closable seal when said seals are in an opened condition, the discharged waste being received within the waste receptacle, and sealed therein by closure of the second seal, and the suit interior being sealed by closure of the first seal, to permit the waste receptacle to be detached from the suit by severing the waste receptacle along the line of weakened material from the upper segment of the waste receptacle.

2. The suit of claim 1 further comprising an upwardly opening storage pocket formed on one of the two pants legs, wherein portions of the waste receptacle are receivable within the storage pocket prior to use in receiving waste.

3. The suit of claim 1 wherein the first closable seal and the second closable seal are formed of mating plastic members which are closable by the application of pressure thereto.

4. The suit of claim 1 wherein a plurality of waste collectors are affixed to the suit outlet.

5. The suit of claim 1 wherein the upper segment of the waste collector is comprised of two flaps, each flap having a concave upper edge which conforms to a shape of an underside of the suit midsection.

6. The suit of claim 1 wherein the waste collector has interior portions which are soft to serve as toilet tissue.

7. A waste collector for attachment to a hazard protection suit having a sealed interior and a midsection with a downwardly opening outlet from the interior, the waste collector comprising:

an upper segment for attachment to the suit midsection to surround the outlet;

an intermediate section which communicates with the upper segment;

a waste receptacle which communicates with the intermediate section;

a first closable seal positioned between the outlet and the intermediate section;

a second closable seal positioned between the intermediate section and the waste receptacle; and portions of the intermediate segment which define a region of weakened material which encircles the intermediate segment to permit the waste receptacle to be detached from the waste collector upper segment, such that waste discharged through the suit outlet and past the first closable seal and the second closable seal when said seals are in an opened condition is received within the waste receptacle, and the first seal and the second seal are closable to retain the suit interior sealed to permit the waste receptacle to be detached from the waste collector by severing the waste receptacle along the line of weakened material from the upper segment of the waste receptacle.

8. The suit of claim 7 wherein the first closable seal and the second closable seal are formed of mating plastic members which are closable by the application of pressure thereto.

9. The suit of claim 7 wherein the upper segment of the waste collector is comprised of two flaps, each flap having a concave upper edge for conformity to a shape of an underside of a hazard protection suit midsection.

10. The suit of claim 1 wherein the waste collector has interior portions which are soft and absorbent to serve as toilet tissue.

11. A method for eliminating human waste from within a sealed interior of a hazard protection suit comprising the steps of:

urinating or defecating within the sealed interior of the hazard protection suit to discharge human waste;

causing the discharged human waste to pass through an outlet in the hazard protection suit;

receiving the discharged human waste which passes through the outlet within a waste collector fixed to the hazard protection suit to seal the outlet, the waste collector having an upper segment which is fixed to the suit, an intermediate section which communicates with the upper segment, and a waste receptacle which communicates with the intermediate section;

after the discharged human waste has been received within the waste receptacle, sealing a first seal positioned outwardly of the suit outlet and positioned between the outlet and the intermediate section and sealing a second seal positioned between the intermediate section and the waste receptacle; and severing the waste receptacle from the intermediate section along portions of the intermediate segment which define a region of weakened material which encircles the intermediate segment between the first seal and the second seal; and removing the severed waste receptacle with the human waste therein and disposing of it.

12. The method of claim 11 further comprising the step of, prior to the urinating or defecating step, storing portions of the waste receptacle within an upwardly opening storage pocket formed on a pants leg of the suit.

13. The suit of claim 11 wherein the step of sealing the first closable seal and the second closable comprises pressing together two opposed mating plastic members making up each seal.

* * * * *